(12) United States Patent
Finnegan

(10) Patent No.: US 10,053,642 B2
(45) Date of Patent: Aug. 21, 2018

(54) METHOD FOR PRODUCING LIGHT RENEWABLE BIOFUEL

(71) Applicant: Verdant Bioproducts Limited, Corby, Northamptonshire (GB)

(72) Inventor: Irene Finnegan, Corby (GB)

(73) Assignee: VERDANT BIOPRODUCTS LIMITED, Milton Keynes (GB)

( * ) Notice: Subject to any disclaimer, the term of this patent is extended or adjusted under 35 U.S.C. 154(b) by 4 days.

(21) Appl. No.: 15/116,710

(22) PCT Filed: Feb. 6, 2015

(86) PCT No.: PCT/GB2015/050328
§ 371 (c)(1),
(2) Date: Aug. 4, 2016

(87) PCT Pub. No.: WO2015/118340
PCT Pub. Date: Aug. 13, 2015

(65) Prior Publication Data
US 2016/0348017 A1    Dec. 1, 2016

(30) Foreign Application Priority Data

Feb. 7, 2014  (GB) .................................. 1402172.9

(51) Int. Cl.
| | | |
|---|---|---|
| *C10L 1/02* | (2006.01) | |
| *C12P 7/62* | (2006.01) | |
| *C12P 5/02* | (2006.01) | |
| *C12P 7/04* | (2006.01) | |
| *C12P 5/00* | (2006.01) | |

(Continued)

(52) U.S. Cl.
CPC ............... *C10L 1/02* (2013.01); *C12P 5/00* (2013.01); *C12P 5/007* (2013.01); *C12P 5/026* (2013.01); *C12P 7/04* (2013.01); *C12P 7/065* (2013.01); *C12P 7/16* (2013.01); *C12P 7/62* (2013.01); *C10L 2200/0469* (2013.01);

(Continued)

(58) Field of Classification Search
CPC combination set(s) only.
See application file for complete search history.

(56) References Cited

U.S. PATENT DOCUMENTS

| | | | | |
|---|---|---|---|---|
| 2009/0324574 A1* | 12/2009 | Mathur | ...................... | C12N 9/14 |
| | | | | 514/1.1 |
| 2016/0348137 A1 | 12/2016 | Finnegan | | |
| 2017/0233773 A1 | 8/2017 | Finnegan | | |

FOREIGN PATENT DOCUMENTS

| | | |
|---|---|---|
| CN | 101603064 A | 12/2009 |
| WO | 2013011292 A2 | 1/2013 |

OTHER PUBLICATIONS

Coban, Esin P. et al, "Evaluation of different pH and temperatures for bacterial cellulose production in HS (Hestrin-Scharmm) medium and beet molasses medium", African Journal of Microbiology Research, vol. 5(9), May 4, 2011, pp. 1037-1045.

(Continued)

*Primary Examiner* — Ellen McAvoy
*Assistant Examiner* — Chantel Graham
(74) *Attorney, Agent, or Firm* — Cantor Colburn LLP

(57) ABSTRACT

There is described a method for producing a biofuel, the method comprising: culturing an *Acetobacter lovaniensis* bacterium in a growth medium containing phosphate at a level which is more than 1 g/liter, wherein culturing of the bacterium produces the biofuel.

24 Claims, 1 Drawing Sheet

(51) Int. Cl.
    *C12P 7/16*  (2006.01)
    *C12P 7/06*  (2006.01)
(52) U.S. Cl.
    CPC ........... *C10L 2290/26* (2013.01); *Y02E 50/10* (2013.01); *Y02E 50/17* (2013.01)

(56) References Cited

OTHER PUBLICATIONS

International Search Report for International Application No. PCT/GB2015/050328; International Filing Date Feb. 6, 2015; dated Jul. 6, 2015; 7 pages.

Written Opinion of the International Searching Authority for International Application PCT/GB2015/050328; dated Jul. 6, 2015; International Filing Date Feb. 6, 2015; Date of Mailing: Jul. 6, 2015; 11 pages.

* cited by examiner

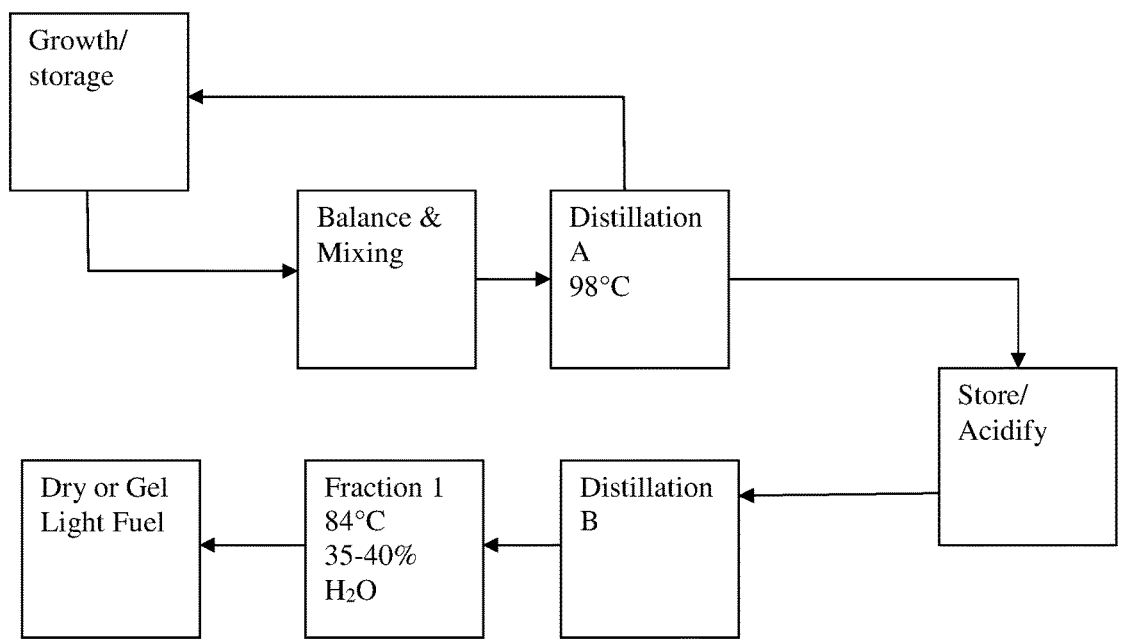

METHOD FOR PRODUCING LIGHT RENEWABLE BIOFUEL

CROSS REFERENCE TO RELATED APPLICATIONS

This application is a National Stage application of International Application No. PCT/GB2015/050328, filed Feb. 6, 2015, which cliams the benefit of GB Application No. 1402172.9, filed Feb. 7, 2014, both of which are incorporated by reference in their entirety herein.

FIELD OF THE INVENTION

The present invention relates to a method for producing a light renewable biofuel by culturing an *Acetobacter* microorganism under particular growth conditions.

BACKGROUND TO THE INVENTION

Over recent years, there has been increasing concern over the consumption of fossil fuels and the production of greenhouse gases. One way to reduce the globe's reliance on fossil fuels has been the development of biofuels from renewable sources. Biofuels such as biopetrol, biodiesel, and bioethanol are considered to be cleaner and more environmentally friendly alternatives to fossil fuels.

Although biofuels may help in reducing greenhouse emissions, they are not without problems. A controversial aspect is the "food for fuel" problem where the demand for energy crops has been perceived as pushing up the prices of grain commodities. Another serious drawback is the damage caused to ecologically sensitive ecosystems, such as rain forests, where the planting of energy crops such as soya and palm has caused large scale destruction.

The biofuels industry is turning to second and third generation biofuels to alleviate these issues. The production of fuels by microorganisms and the use of waste substrates are important areas of research.

The conversion of carbon dioxide to fuel molecules is known. Carbon dioxide can be converted chemically, electrochemically, and either directly or indirectly by microorganisms.

WO2013/011292 describes a microorganism which is capable of producing long chain aliphatic carboxylic acids by fixing carbon dioxide to produce formate, and then sequentially adding carbon atoms to the backbone to produce the long chain aliphatic carboxylic acids. This document describes a particular strain referred to as *Acetobacter lovaniensis* FJ1 having accession number NCIMB 41808 (deposited at NCIMB Ltd. (Ferguson Building, Craibstone Estate, Bucksburn, Aberdeen, AB21 9YA) on 12 Jan. 2011 under the provisions of the Budapest Treaty).

SUMMARY OF THE INVENTION

It has been surprisingly found that the *Acetobacter lovaniensis* strain described in WO2013/011292 can produce an alternative range of products, such as alcohols, esters and monoterpenes, when grown on a phosphate enriched growth regime. It is believed that a metabolic switch occurs under such growth conditions. It was not previously known that this microorganism could produce such products. Therefore, the present invention relates to a method for producing a biofuel using the microorganism described in WO2013/011292. The disclosure of WO2013/011292 is incorporated herein in its entirety.

In a first aspect, the present invention provides a method for producing a biofuel, the method comprising: culturing an *Acetobacter lovaniensis* bacterium in a growth medium containing phosphate at a level which is more than 1 g/liter, wherein culturing of the bacterium produces the biofuel.

The *Acetobacter lovaniensis* bacterium in cultured in a growth medium containing more than 1 g/liter of phosphate. 1 g/liter is the amount of phosphate ion ($PO_4^{3-}$) in the growth medium rather than the amount of the phosphate containing compound in the growth medium. For example, potassium dihydrogen phosphate ($KH_2PO_4$) has a relative molecular mass of 136. The phosphate part of this has a relative molecular mass of 95. Therefore, if 136 grams of $KH_2PO_4$ was added to 100 liters of water, there would be 1.36 g/liter of $KH_2PO_4$ in the water but there would be 0.95 g/liter of phosphate in the water.

In some embodiments, the growth medium preferably contains phosphate at a level which is more than 2 g/liter. In other embodiments, the growth medium contains phosphate at more than 3 g/liter. In further embodiments, the growth medium contains phosphate at more than 4 g/liter. In particular embodiments, the growth medium contains phosphate at more than 5 g/liter. In some embodiments, the growth medium contains phosphate at more than 6 g/liter. In other embodiments, the growth medium contains phosphate at more than 7 g/liter. In further embodiments, the growth medium contains phosphate at more than 8 g/liter. In particular embodiments, the growth medium contains phosphate at more than 9 g/liter. In some embodiments, the growth medium contains phosphate at more than 10 g/liter. In other embodiments, the growth medium contains phosphate at more than 11 g/liter. In further embodiments, the growth medium contains phosphate at more than 12 g/liter. In a preferred embodiment, the growth medium contains phosphate at more than 13 g/liter. In another preferred embodiment, the growth medium contains phosphate at more than 14 g/liter.

In some embodiments, the growth medium contains phosphate at a level which is less than 150 g/liter. In other embodiments, the growth medium contains phosphate at less than 100 g/liter. In further embodiments, the growth medium contains phosphate at less than 80 g/liter. In various embodiments, the growth medium contains phosphate at less than 70 g/liter. In particular embodiments, the growth medium contains phosphate at less than 60 g/liter. In some embodiments, the growth medium contains phosphate at less than 50 g/liter. In other embodiments, the growth medium contains phosphate at less than 45 g/liter. In further embodiments, the growth medium contains phosphate at less than 40 g/liter. In particular embodiments, the growth medium contains phosphate at less than 35 g/liter. In some embodiments, the growth medium contains phosphate at less than 30 g/liter. In other embodiments, the growth medium contains phosphate at less than 25 g/liter. In further embodiments, the growth medium contains phosphate at less than 20 g/liter. In particular embodiments, the growth medium contains phosphate at less than 15 g/liter.

In some embodiments, the growth medium contains phosphate at a level which is between 1 and 150 g/liter. In other embodiments, the growth medium contains phosphate at between 2 and 100 g/liter. In further embodiments, the growth medium contains phosphate at between 3 and 80 g/liter. In various embodiments, the growth medium contains phosphate at between 4 and 70 g/liter. In particular embodiments, the growth medium contains phosphate at between 5 and 60 g/liter. In some embodiments, the growth medium contains phosphate at between 6 and 50 g/liter. In other embodiments, the growth medium contains phosphate at between 7 and 45 g/liter. In further embodiments, the growth medium contains phosphate at between 8 and 40 g/liter. In particular embodiments, the growth medium contains phosphate at between 9 and 35 g/liter. In some embodiments, the growth medium contains phosphate at between 10 and 30 g/liter. In other embodiments, the growth medium contains phosphate at between 11 and 25 g/liter. In further embodiments, the growth medium contains phosphate at between 12 and 20 g/liter. In particular embodiments, the growth medium contains phosphate at between 13 and 15 g/liter.

The growth medium can be any suitable growth medium which allows the *Acetobacter lovaniensis* bacterium to grow and reproduce, and to produce the biofuel. The growth medium may contain various ingredients/nutrients to allow the bacterium to grow and reproduce. The growth medium may contain one or more of the following additives: a potassium salt, a magnesium salt, a manganese salt, an iron salt, a copper salt, a cobalt salt, a sodium salt, a zinc salt, a calcium salt, a molybdenum salt, a chloride, a sulphate, a molybdate and a carbonate. These additives are generally present in the growth medium at between 0.01 and 2 g/liter.

In some embodiments, the growth medium may have one or more of the following additives in the amount specified:

| Ingredient | g/1000 ml |
| --- | --- |
| Potassium Hydrogen Phosphate | 10-30 |
| Magnesium Chloride | 0.1-2 |
| Manganese Chloride | 0.01-0.1 |
| Ferric Chloride | 0.01-0.1 |
| Copper Sulphate | 0.01-0.1 |
| Cobalt Chloride | 0.01-0.1 |
| Sodium molybdate | 0.01-0.1 |
| Zinc Chloride | 0.1-1 |

In a particular embodiment, the growth medium has the following composition:

| Ingredient | g/1000 ml |
| --- | --- |
| Potassium Hydrogen Phosphate | 20 |
| Magnesium Chloride | 1 |
| Manganese Chloride | 0.05 |
| Ferric Chloride | 0.05 |
| Copper Sulphate | 0.05 |
| Cobalt Chloride | 0.05 |
| Sodium molybdate | 0.05 |
| Zinc Chloride | 0.5 |

Preferably, the growth medium does not contain an exogenous source of nitrogen. This is not required as the bacterium can fix nitrogen which is dissolved in the growth medium from the atmosphere.

The bacterium can fix carbon dioxide. Therefore, the growth medium does not require an exogenous source of carbon other than carbon dioxide dissolved in the growth medium from the atmosphere. However, in some embodiments, before the bacterium is cultured or during culturing, carbon dioxide can be bubbled through the growth medium to increase the amount of carbon dioxide dissolved in the growth medium. The bacterium can use carbon dioxide as the sole source of carbon.

In some embodiments, glycerol is added to the growth medium as an additional source of carbon. Preferably, this is done after the bacterium has started to grow and reproduce.

The growth medium may have a pH of between 3.5 and 9. Preferably, the growth medium has a pH of between 4 and 7. In a particular embodiment, the pH of the growth medium is about 4.5.

The growth medium is preferably aqueous such that the nutrients/additives are dissolved in water.

The bacterium is generally cultured at a temperature of between 0° C. and 60° C. Preferably, the bacterium is cultured at a temperature of between 10° C. and 40° C. In some embodiments, the bacterium is cultured at a temperature of between 15° C. and 30° C.

The bacterium is generally cultured until the growth culture reaches an optical density when measured at 600 nm ($OD_{600}$) of between 0.75 and 1.00.

During culturing, the culture can be diluted with additional growth medium to increase the volume of culture. Therefore, when it is desired to extract the biofuel, the culture should have a final optical density of between 0.75 and 1.00.

The bacterium may be cultured for between 12 and 36 hours. In some embodiments, the bacterium may be cultured for between 18 hours and 30 hours.

The biofuel is produced by culturing an *Acetobacter lovaniensis* bacterium. The bacterium can be any suitable *Acetobacter lovaniensis* bacterium which can produce the biofuel. This includes strain FJ1 (having accession number NCIMB 41808) and similar strains which are related to or derived from FJ1. The term "derived from" means that FJ1 can be modified or mutated to produce further bacteria. For example, genes may be inserted or removed from FJ1. Bacteria which are derived from FJ1 should be functionally equivalent to FJ1 and should be able to produce a biofuel. Further, the derived bacterium should be able to grow under the same conditions as FJ1. Preferably, the bacterium is strain FJ1 having accession number NCIMB 41808. A bacterium can be identified as an *Acetobacter lovaniensis* bacterium by methods which are well known to those skilled in the art, for example, by using 16S rDNA analysis.

The bacterium produces the biofuel as it grows so once the culturing of the bacterium has been completed, the biofuel will be present in the growth medium. The biofuel can then be extracted, if desired.

The term 'biofuel' means combustible molecules which can be used as a fuel and burnt to release energy. The biofuel produced by the method of the invention includes volatile alcohols, esters and monoterpenes.

The method may further comprise the step of separating the biofuel from the growth medium. This can be in a first separation step. This can be done in any suitable way and a number of methods will be apparent to one skilled in the art.

For example, the biofuel can be separated using distillation, including standard distillation, fractional distillation, vacuum distillation, distillation with an entrainer, solvent extraction followed by recovery with distillation, and continuous distillation. Other separation methods include membrane perfusion, electro-chemical separation, or the use of critical carbon dioxide.

If distillation is carried out at 1 atmosphere (rather than at reduced pressure as in vacuum distillation) using, for example, a side arm condenser, the biofuel will be contained in the first 10% of the distillate. Generally, this initial distillate will be collected at a temperature of between 95° C. and 100° C., in particular, at about 98° C. Typically, the biofuel is collected as part of an azeotrope.

Once the biofuel has been separated, it may be acidified by adding an acid to the biofuel. Suitable acids include hydrochloric acid and sulphuric acid. The pH may be reduced to 5 or below, or preferably 4.5 or below. This helps in further separation steps in that the azeotrope formed in Distillation A 'breaks' and releases the light fractions of the biofuel.

A second separation step can take place to further separate/purify the biofuel from any other products which are present. This second separation can be carried out using any suitable method. For example, the biofuel can be separated using distillation, including standard distillation, fractional distillation, vacuum distillation, distillation with an entrainer, solvent extraction followed by recovery with distillation, and continuous distillation. Other separation methods include membrane perfusion, electro-chemical separation, or the use of critical carbon dioxide.

If distillation is carried out at 1 atmosphere (rather than at reduced pressure as in vacuum distillation) using, for example, a fractionating column, the biofuel will distil at a temperature of between 70° C. and 90° C., typically at about 85° C. This is normally the first fraction.

Once separated, the biofuel may be dried to remove some of the water. This can be done with agents such as, but not limited to, chloride salts (calcium or sodium) or molecular sieve 3 A.

The biofuel can then be further processed, if desired, to further separate particular components of interest or to modify the characteristics of the biofuel. For example, the method may optionally comprise one or more of the following steps:
1) separating particular components of the biofuel;
2) filtering the biofuel;
3) blending the biofuel with a different fuel such as bioethanol or petrol;
4) chemically modifying the biofuel; and
5) distilling off certain fractions of the biofuel.

In a particular embodiment, there is provided a method for producing a biofuel, the method comprising:
culturing *Acetobacter lovaniensis* strain FJ1 having accession number NCIMB 41808 in a growth medium containing phosphate at a level which is between 10 and 30 g/liter, wherein culturing of the bacterium produces the biofuel; and
separating the biofuel from the growth medium.

In this embodiment, the phosphate level is described as being between 10 and 30 g/liter. However, any of the levels described above can be used in this particular embodiment. For example, the phosphate level may be more than 1 g/liter or the phosphate level may be between 13 and 15 g/liter, or any of the embodiments in between.

The products produced by the bacterium include a series of volatile alcohols, esters and monoterpenes. These molecules have potential as biofuels.

Among compounds of interest produced by the bacterium are alcohols including ethanol, butanol, pentanol and 4-methyl pentanol. Alcohols such as ethanol are used as petrol substitutes or for blending with petrol. Petrol has an energy density of 32 MJ/l and ethanol an energy density of 21 MJ/l. Pentanol isomers are advantageous when compared to ethanol in that they have energy densities of around 28 MJ/l and much lower affinities for water.

Therefore, the method may involve separating the alcohols from the biofuel. This can be done by in any suitable way and suitable methods, such as distillation, would be apparent to someone skilled in the art.

Also synthesised are a number of ester molecules including butyl acetate. Butyl acetate is a known petrol additive which is an octane booster. This molecule is also a potential renewable biofuel additive.

Therefore, the method may involve separating the ester molecules from the biofuel. This can be done by in any suitable way and suitable methods, such as distillation, would be apparent to someone skilled in the art.

Further compounds of interest produced by the bacterium are monoterpenes including α-terpineol, γ-terpineol, γ-terpinene, D-limonene and eucalyptol. Monoterpenes are C10 isoprenoids which show great potential as replacement molecules for petrol and after further catalytic hydrogenation replacements for jet and rocket fuels. Isoprenoids and their hydrogenation products are known fuels.

Therefore, the method may involve separating the monoterpenes from the biofuel. This can be done by in any suitable way and suitable methods, such as distillation, would be apparent to someone skilled in the art.

The monoterpenes may be subjected to further processing such as hydrogenation.

The present invention also provides a biofuel produced by the method described above.

Further, the present invention provides the use of the biofuel or a component thereof, for example, as an additive, as described above.

It is thought that the enzymes responsible for producing the biofuel are extracellular of the bacterium. These enzymes function regardless of whether the cells of the bacterium are present. Therefore, in another aspect of the invention, there is provided a method for producing a biofuel, the method comprising: providing an aqueous medium containing a cell-free extract of an *Acetobacter lovaniensis* bacterium cultured in a growth medium containing phosphate at a level which is more than 1 g/liter, wherein the biofuel is produced in the aqueous medium.

The steps described above for the method of the first aspect of the invention, for example, relating to separating the biofuel, etc. are equally applicable to this aspect of the invention.

The medium can be produced by culturing the bacterium for a period of time to allow the enzyme systems to be produced in the medium. The cell-free extract can be prepared by removing the cells of the bacterium from the medium after culturing, for example, by repeated ultra-filtration.

In a further aspect of the invention, there is provided an aqueous medium containing a cell-free extract of an *Acetobacter lovaniensis* bacterium cultured in a growth medium containing phosphate at a level which is more than 1 g/liter.

DETAILED DESCRIPTION OF THE INVENTION

The invention will now be described in detail by way of example only with reference to the FIGURES in which:

FIG. 1 is a flow diagram showing the synthesis of biofuel by *Acetobacter lovaniensis* FJ1 (growing on carbon dioxide in the presence of elevated levels of phosphate) and its subsequent recovery.

OVERVIEW

In the presence of enriched levels of phosphate, and optionally in the absence of an exogenous source of nitrogen and carbon, *Acetobacter lovaniensis* FJ1 produces a different set of metabolites.

Without wishing to be held to a particular theory, it is thought that there is a metabolic switch to carbon dioxide fixation via the hydroxyl propionate cycle (Tabita, F. J., PNAS (2009), 106, 21015-21016; Strauss, G. And Fuchs.

G., Eur. J. Biochem (1993), 215, 633-643) in the presence of elevated levels of phosphate. In addition, nitrogen fixation via a nitrogenase enzyme type complex results in the generation of hydrogen (Tamagnini P., Axelssen R., Lindberg P., Oxelfelt F., Wenschiers R. and Lindblad P., Microbiology and Molecular Biology Reviews (2002), 66, 11-20) which is utilised by hydrogenase enzymes and balances the redox system of the organism. While carbon and nitrogen assimilation has been noted in other organisms (Levican G., Ugalde J. A., Ehrenfeld M., Maass A., and Parada P., BMC Genomics (2008), 581, 1186; Dubbs J. M. and Tabita F. R., Fems Microbiol Rev. (2004), 28, 353-356; McKinlay J. B. and Harwood C. S., PNAS (2010), 1073, 1-7), the use of carbon dioxide fixation as a redox recycling mechanism via a nitrogenase system has only been previously noted in anoxygenic phototrophic bacteria such as non-sulphur purple bacteria where the carbon dioxide is reduced via the Calvin Benson Basham cycle. *Acetobacter* species may be able to take advantage of this effect.

Process for Producing Biofuel

*Acetobacter lovaniensis* FJ1 (accession number: NCIMB 41808) is grown on a minimal salt media in which sources of nitrogen are excluded and which the level of phosphate elevated. The composition of this media is shown in the table below.

TABLE 1

Composition of Minimal Salt Media Used to Grow *Acetobacter Lovaniensis* FJ1

| Ingredient | g/1000 ml |
|---|---|
| Potassium Hydrogen Phosphate | 20.00 |
| Magnesium Chloride | 1.00 |
| Manganese Chloride | 0.05 |
| Ferric Chloride | 0.05 |
| Copper Sulphate | 0.05 |
| Cobalt Chloride | 0.05 |
| Sodium molybdate | 0.05 |
| Zinc Chloride | 0.50 |

The media is dissolved in water and filtered. The water used can be either distilled water or tap water. The microorganism can be grown under non-sterile conditions and further sterilisation of media and equipment either by autoclaving or some other suitable method is not required.

The microorganism is inoculated into two liter quantities of media in shake flasks or other suitable containers and grown to an A600 of between 0.75 and 1.00. Two liters of culture media is then diluted in fresh media to a volume of 10 liters and again cultured to an A600 of between 0.75 and 1.0. The volume of the culture media is increased to the desired volume by repeated splitting of the culture.

The spent bacterial media can be stored for extended periods of time of up to twelve months.

The spent bacterial media is distilled to recover products of interest using the general process shown in FIG. 1.

A standard distillation set can be used employing a flask, heater mantle, with or without fractionation column and distillation head with condenser. However, other methods of distillation such as vacuum distillation, distillation with an entrainer, solvent extraction followed by recovery with distillation and continuous distillation are also applicable. Other procedures for the recovery of metabolites such as membrane perfusion, electro-chemical separation, or recovery through the use of critical carbon dioxide can also be employed.

The distilled biofuel can be acidified. This can help in the further separation of biofuel components. For example, acidification can be used to catalyse the conversion of esters into carboxylic acids and alcohols. The alcohols can then be separated (with or without other components). For example, any ethanol can be distilled off at around 84° C.

Individual products can be identified using mass spectroscopy with and without derivatization depending on the source and type of sample. For samples where derivatization is required, material is extracted into a suitable solvent and then treated with BSTFA (N,O-bis(trimethylsilyl)trifluoro-acetamide) and TMS (trimethylsilyl). The instrument is typically run with an injection temperature of 80° C. followed by a 7° C. per minute rise to reach a full temperature of 300° C. The column is then held for 5 minutes at this temperature. A basic library search was used to identify the peaks.

EXAMPLES

Example 1

The Growth of Organism in the Absence of Exogenously Added Nitrogen and on Carbon Dioxide as Sole Source of Carbon The organism typically has a 72 hour growth cycle when grown in the presence of elevated levels of phosphate and achieves 0.07 g/l/h dry cell weight at 20° C.

Example 2

The Production of Biofuel by a Simple Two Step Distillation Process

The biofuel can be recovered in a simple two step distillation process.
1. Spent bacterial media is distilled in a simple distillation pot without a fractionation column but employing a side arm condenser. The biofuel fractions are collected in the first 10% of the distillate. This is "Distillation A".
2. Pooled fractions from Distillation A are re-distilled in a distillation unit employing a 10 liter reaction flask and a packed fractionation column. Prior to distillation the pooled fraction from Distillation A is acidified with a suitable mineral acid. In Distillation B, the initial 5% containing ethanol and other volatile fractions is then removed at between 75° C. and 85° C. (Fraction 1). This fraction is the biofuel. This product may then be further processed or separated, if desired, or used as a stand alone fuel.

Additives may be added to the biofuel. Additives such as anti-oxidants, oxygenates, thermal stability improvers, stabilizers, cold flow improvers, combustion improvers, anti-foam additives, anti-haze additives, corrosion inhibitors, lubrication improvers, anti-icing inhibitors, injector cleanliness additives, smoke suppressants, drag reducing additives, metal deactivators, dispersants, detergents, demulsifying agents, dyes, markers, static dissipaters, biocides, cetane improvers may be required dependant on the fuel type.

The "stand alone" fuel, meaning the crude fraction (Fraction 1) collected at 70-85° C., can be used without further separation into individual components. The fuel can be used as such in generators, heaters, burners, combined heat and power engines, internal combustion engines such as petrol engines after the water content has been reduced to an acceptable level.

Fraction 1 can be used in simple burners such as those currently used to burn bioethanol for light, heat and cooking. The fuel can ignite in the presence of up to 30% water and such can be employed as an emulsion or gel. The fuel can be mixed with gelling agents such as, but not limited to calcium acetate to improve the safety of the product if spilt. The fuel can be used in combination with additives as described above for use in a variety of more sophisticated engines such as combined heat and power engines, generators and other internal combustion engines such as petrol engines.

Fraction 1 can be further separated by fractional distillation or distillation under reduced pressure to yield its alcohol fraction. The alcohol fraction comprises pentanol and 4-methylpentanol. This fraction can be used as a fuel in combination with additives suitable for the application as a fuel or in combination with petrol as a blended fuel.

Fraction 1 can be further separated by fractional distillation or distillation under pressure to yield its ester fraction. This fraction consists of butyl acetate. Butyl acetate can be used as an octane booster either with conventional fuels such as petrol, renewable fuels such as fatty acid methyl esters and hydrogenated isoprenoids and in combination with individual components of Fraction 1.

Fraction 1 can be further separated by fractional distillation or distillation under pressure to yield its isoprene or monoterpene fraction. This fraction can be further hydrogenated to produce fuel types suitable for liquid missile, jet, petrol and diesel engines. Hydrogenation can be effected with hydrogen gas in the presence of a suitable catalysts such as platinum, palladium or Raney nickel. Elevated temperatures and pressures are variously used to carry out the hydrogenation reaction. Alternatively, the monoterpene fraction can be reduced using hydrazine in the presence of 5-ethyl-methylumflavin perchlorate as catalyst. An alternative catalyst such as lithium aluminium hydride can be employed to effect reduction. The monoterpene constituents can be reduced after separation or as a crude fraction. Additives as described above can be used in various combinations as suitable for a particular fuel type. For example, whereas a petrol fuel requires an octane booster, a diesel type fuel requires a cetane booster.

The properties of an exemplary biofuel produced by the above method are as follows:

| TEST | TEST METHOD | RESULT |
| --- | --- | --- |
| WATER % | ASTM D1744-83 | 21.98 |
| FLASH POINT ° C. | ASTM D1310-86 | 16.0 |
| DENSITY @ 20° C. kg/l | ASTM D4052-86 | 846.2 |
| COPPER STRIP CORROSION @ 50° C. | ASTM D130-88 | 1b PASS |
| VISCOSITY @ 40° C. | ASTM D445-88 | 0.9758 |
| VISCOSITY @ 20° C. |  | 1.371 |
| OXIDATIVE STABILITY INDUCTION PERIOD H | ASTM D525-88 | 8 |
| FREEZING POINT ° C. | ASTM D7154 |  |
| 10.95% WATER |  | LESS THAN −45 |
| 21.98% WATER |  | LESS THAN −45 |
| 57.00% WATER |  | LESS THAN −45 |
| 87.80% WATER |  | LESS THAN −45 |

The invention claimed is:

1. A method for producing a biofuel, the method comprising:
culturing an *Acetobacter lovaniensis* bacterium in a growth medium containing phosphate at a level which is more than 1 g/liter to produce a biofuel comprising volatile alcohols, esters and monoterpenes, and separating the biofuel comprising volatile alcohols, esters and monoterpenes from the growth medium.

2. The method of claim 1, wherein the growth medium contains phosphate at more than 10 g/liter.

3. The method of claim 1, wherein the growth medium contains phosphate at more than 13 g/liter.

4. The method of claim 1, wherein the growth medium contains phosphate at between 10 and 30 g/liter.

5. The method of claim 1, wherein the growth medium does not contain an exogenous source of nitrogen.

6. The method of claim 1, wherein the growth medium does not contain an exogenous source of carbon.

7. The method of claim 1, wherein the growth medium contains glycerol.

8. The method of claim 1, wherein the growth medium has a pH of between 4 and 7.

9. The method of claim 1, wherein the bacterium is cultured at a temperature of between 15° C. and 30° C.

10. The method of claim 1, wherein the bacterium is cultured until the growth medium reaches an $OD_{600}$ of between 0.75 and 1.00.

11. The method of claim 1, wherein the bacterium is strain FJ1 having accession number NCIMB 41808.

12. The method of claim 1, wherein the method further comprises a step of acidifying the separated biofuel.

13. The method of claim 1, wherein the method further comprises a second step of separating the biofuel.

14. The method of claim 1, wherein the method further comprises the step of drying the biofuel.

15. The method of claim 1, wherein the method further comprises a step of extracting one or more individual components from the biofuel.

16. The method of claim 1, wherein the method further comprises the step of chemically modifying or processing the biofuel or one or more individual components.

17. The method of claim 16, wherein the method further comprises the step of adding one or more additives to the biofuel, to the one or more individual components, or to the chemically modified or processed biofuel or one or more individual components.

18. The method of claim 1, wherein the method further comprises a step of extracting alcohols, esters or monoterpenes from the biofuel.

19. The method of claim 1, the method comprising:
culturing *Acetobacter lovaniensis* strain FJ1 having accession number NCIMB 41808 in a growth medium containing phosphate at a level which is between 2 and 100 g/liter, wherein culturing of the bacterium produces the biofuel;
separating the biofuel from the growth medium.

20. The method of claim 1, wherein the method comprises one or more of the following steps:
1) separating particular components of the biofuel;
2) filtering the biofuel;
3) blending the biofuel with a different fuel such as bioethanol or petrol;
4) chemically modifying the biofuel;
5) distilling off certain fractions of the biofuel; and
6) drying the biofuel.

21. A method for producing a biofuel, the method comprising:
providing an aqueous medium containing a cell-free extract of an *Acetobacter lovaniensis* bacterium cultured in a growth medium containing phosphate at a level which is more than 1 g/liter, wherein a biofuel comprising volatile alcohols, esters and monoterpenes is produced in the aqueous medium; and optionally separating the biofuel from the aqueous medium.

22. An aqueous medium containing a cell-free extract of an *Acetobacter lovaniensis* bacterium cultured in a growth medium containing phosphate at a level which is more than 1 g/liter.

23. A biofuel produced by the method according to claim 1, wherein the biofuel comprises volatile alcohols, esters and monoterpenes.

24. The method of claim 1, further comprising using the biofuel or a component thereof as an additive.

* * * * *